April 7, 1936. J. H. NICOLAS Plant Pat. 172
ROSE
Filed Nov. 19, 1935
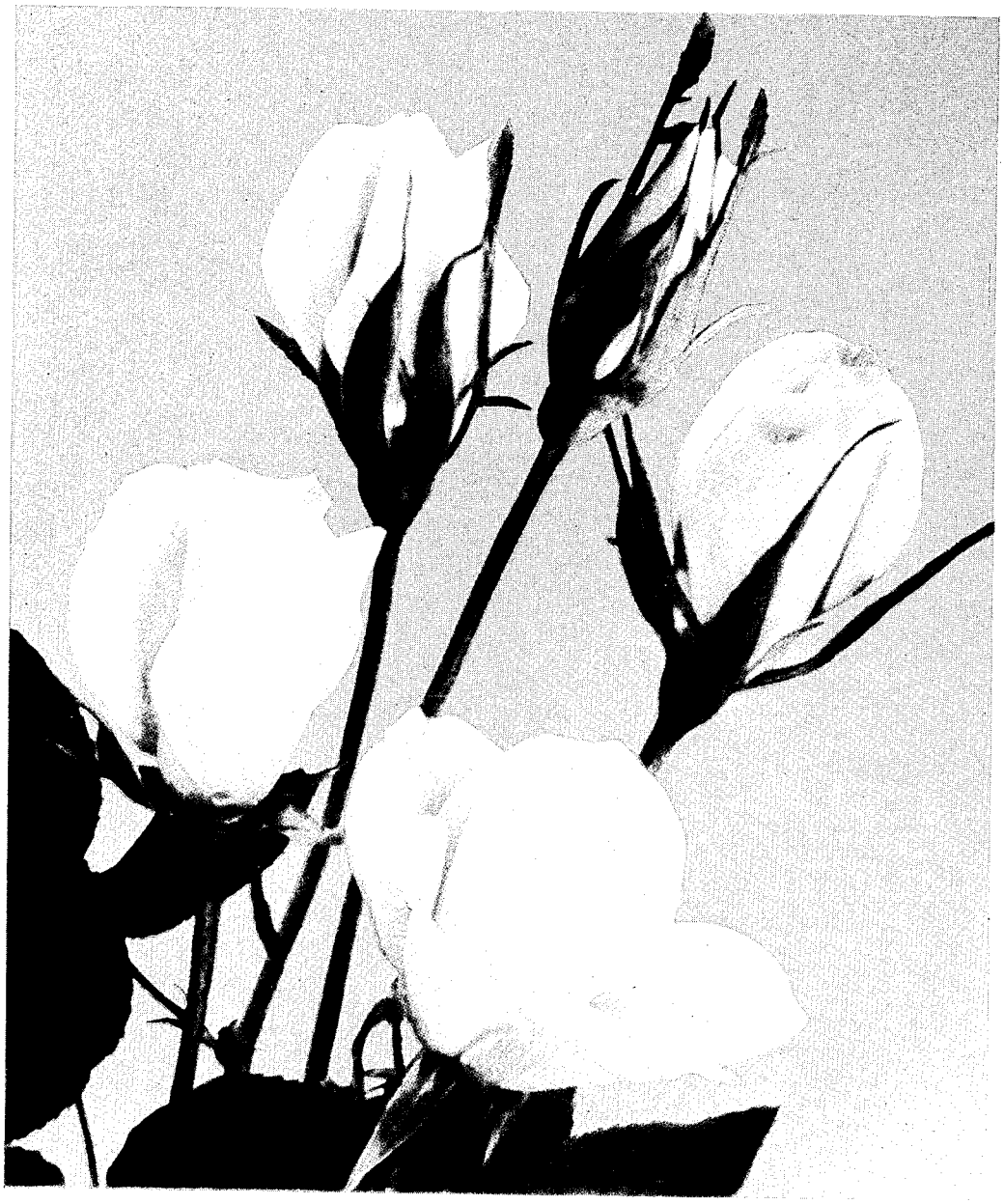
Inventor
J. H. Nicolas
By Robb & Robb
Attorneys Patented Apr. 7, 1936

Plant Pat. 172

UNITED STATES PATENT OFFICE

172

ROSE

Jean H. Nicolas, Newark, N. Y., assignor to Jackson & Perkins Company, Newark, N. Y.

Application November 19, 1935, Serial No. 50,593

1 Claim. (Cl. 47—61)

The present invention relates to a new and distinct variety of rose plant, the result of a definite effort primarily to impart new vigor into the cut flower type of rose and at the same time reinforce, so to speak, the color of its bloom.

I have found that as a result of the hybridizing, not only were the foregoing objectives achieved, but an entirely new type, or strain, of forcing rose has been produced. Furthermore, extensive trials have demonstrated that this new rose forms an important addition to the garden rose line as it retains outdoors the characteristics and features which distinguish it under glass.

The purpose of selecting for its pollen parent the variety "Federico Casas", a second generation seedling of Frau Karl Druschki (Pernetiana seedling x (Frau Karl Druschki x Rayon d'Or), was to obtain the advantage of the exceptional vigor, upright habit and rich pigmentation which characterize this known rose while the seed parent Joanna Hill was selected because it is today the most used among yellow forcing roses.

The result of this cross exhibits as its main character the extremely long, slender "streamline" bud which under intensive greenhouse culture may reach up to three inches in length and sheathed in long sepals generally forming a "bonnet" above the bud branching like anthers.

In color, the bud is a combined rich gold and saffron, very lasting and changing but little, the petals being very thick and resembling kid leather in toughness.

The foliage of this new variety is also distinct and of a new type, rather elongated, thick and of a deep flat green. The foliage is also plentiful and the nodes between leaves very short.

The production of commercial flowers under glass has been found to be very large, exceeding that of the well-known "Talisman", and this from the commercial standpoint lends extreme value to the new variety as revolutionary in the yellow cut rose industry.

From several years of testing and experimentation, the characteristics herein set forth have been demonstrated to be fixed in asexual propagation.

The following is a detail description of the new variety, reference to color according with the Gravereaux color chart:—

Parentage:
- Seedling.
- Seed parent—Joanna Hill.
- Pollen parent—Federico Casas.

Classification:
- Botanic—Pernetiana Hybrid.
- Commercial—Hybrid Tea.

*Flower*

Blooming habit:
- Location where observations were made, greenhouses and fields at Newark, N. Y.
- Continuous.

Bud:
- *Size.*—Slender.
- *Form.*—Very long; pointed; unaffected by wet or hot weather.
- *Color.*—When sepals first divide—saffron. When petals begin to unfurl—same. When half blown: inside of petals—gold, reverse side of petals—saffron.
- *Sepals.*—Branched, "hood" above bud. Stand up.
- *Calyx.*—Shape — funnel. Size — slender. Aspect—smooth.
- *Peduncle.* — Length — very long. Aspect — smooth. Color—medium. Strength—erect, slender.
- *Opening.*—Opens well and is unaffected by adverse conditions.

Bloom:
- *Size.*—Large; average size when fully expanded 4½ inches.
- *Borne.*—Singly.
- *Stems.*—Long; strong.
- *Form.*—When first opened cupped.
- *Permanence.*—Flattens.
- *Petalage.*—Double (full but open center). Number of petals under normal conditions varies from 20 to 30 according to season.
- *Color.*—Center of flower—saffron. Outer petals—gold. Base of petals (aiglet)—lighter yellow. Inside of petals—saffron. Reverse side of petals—gold. General tonality from a distance—rich gold.
- *Variegations.*—None.
- *Discoloration.*—General tonality at end of first day—saffron. Second day—gold. Third day—lighter yellow.

Petals:
- *Texture.*—Thick; unaffected by wet or hot weather.
- *Appearance.*—Inside and outside shiny.
- *Form.*—Round.
- *Arrangement.*—Imbricated (regularly arranged) shingle-like; no petaloids in center.
- *Persistence.*—Drop off cleanly.
- *Fragrance.* — Strong. Nature—Tea (average hybrid tea scent).

*Lasting quality.*—On plant and as cut flower very long.

Genital organs:

*Stamens, anthers.*—Large, many. Color—yellow. Arrangement—regular around styles.

*Stamens, filaments (threads).*—Long. Color—reddish.

*Pollen.*—Lemon yellow.

*Styles.*—Bunched; uneven length; long; heavy.

*Stigmas.*—Color—white.

*Ovaries.*—Some protruding from calyx.

Fruit:

Variety is fertile with its own pollen.

*Form.*—Pear shaped, seeds protruding generally.

*Aspect.*—Smooth.

*Color at maturity.*—Russet brown.

*Sepals.*—Caducous (soon falling).

*Plant*

Form:

Bush.

Growth:

Very vigorous, upright.

Foliage:

Five and often seven leaflets.

*Size.*—Medium.

*Quantity.*—Abundant.

*Color.*—New foliage—upper side—bronzy, under side—bronzy. Old foliage—upper side—dark green, under side—lighter green.

*Shape.*—Lanceolate.

*Texture.*—Upper side leathery. Under side rough. Ribs and veins ordinary.

*Edge.*—Serrated (saw toothed).

*Serrations.*—Single; sharp.

*Rachis.*—Color green, under side prickles.

*Stipules.*—Long, smooth.

*Disease resistance.*—Resistant.

Wood:

*New wood.*—Reddish color. Bark—rough.

*Old wood.*—Green color. Bark—rough.

Thorns: (Divided into Thorns, Prickles and Short needles).

*Thorns.*—Quantity—on main stalks from base, ordinary; on laterals from stalk, few. Form—broad base; medium; straight. Color when young—red. Position—irregular.

*Prickles.*—Quantity—on main stalks, few; on laterals, few. Color—brown.

*Short needles.*—Quantity—on main stalks, few; on laterals, few.

I claim:

The new and distinct variety of rose plant, characterized by the vigorous, upright, growing habit of the plant, the form and color of its foliage, and the color and structure of the bud and flower, distinguishing the plant as a new type of forcing rose adaptable for either cut flower or garden purposes, substantially as shown and described.

JEAN H. NICOLAS.